US011298392B2

(12) United States Patent
Cheng et al.

(10) Patent No.: US 11,298,392 B2
(45) Date of Patent: Apr. 12, 2022

(54) METHOD FOR TREATING GLIOBLASTOMA MULTIFORME

(71) Applicant: Da-Tong Ju, Taipei (TW)

(72) Inventors: Wei-Te Cheng, New Taipei (TW); Chen-Yu Lee, Taipei (TW); Yan-Chih Liao, Taipei (TW); Chi-Tun Tang, Taipei (TW); Chuang-Hsin Chiu, Taipei (TW); Hsin-I Ma, New Taipei (TW); Da-Tong Ju, Taipei (TW); Tung-Han Tsai, Kaohsiung (TW)

(73) Assignee: Da-Tong Ju, Taipei (TW)

( * ) Notice: Subject to any disclaimer, the term of this patent is extended or adjusted under 35 U.S.C. 154(b) by 63 days.

(21) Appl. No.: 17/010,871

(22) Filed: Sep. 3, 2020

(65) Prior Publication Data

US 2022/0062363 A1  Mar. 3, 2022

(51) Int. Cl.

| A61K 36/324 | (2006.01) |
| A61K 36/232 | (2006.01) |
| A61K 36/236 | (2006.01) |
| A61K 36/64 | (2006.01) |
| A61K 36/65 | (2006.01) |
| A61K 36/736 | (2006.01) |
| A61K 36/286 | (2006.01) |
| A61K 36/35 | (2006.01) |
| A61K 36/11 | (2006.01) |
| A61K 36/21 | (2006.01) |
| A61K 36/539 | (2006.01) |
| A61K 36/718 | (2006.01) |
| A61K 36/756 | (2006.01) |
| A61K 36/07 | (2006.01) |
| A61K 36/884 | (2006.01) |
| A61K 36/284 | (2006.01) |
| A61K 36/8988 | (2006.01) |
| A61K 36/75 | (2006.01) |
| A61K 36/13 | (2006.01) |
| A61K 36/237 | (2006.01) |
| A61K 36/233 | (2006.01) |
| A61K 36/752 | (2006.01) |
| A61K 36/88 | (2006.01) |
| A61K 36/258 | (2006.01) |
| A61K 36/714 | (2006.01) |
| A61K 36/61 | (2006.01) |
| A61K 36/605 | (2006.01) |
| A61K 36/484 | (2006.01) |
| A61K 36/328 | (2006.01) |

(52) U.S. Cl.
CPC ............ *A61K 36/324* (2013.01); *A61K 36/07* (2013.01); *A61K 36/11* (2013.01); *A61K 36/13* (2013.01); *A61K 36/21* (2013.01); *A61K 36/232* (2013.01); *A61K 36/233* (2013.01); *A61K 36/236* (2013.01); *A61K 36/237* (2013.01); *A61K 36/258* (2013.01); *A61K 36/284* (2013.01); *A61K 36/286* (2013.01); *A61K 36/328* (2013.01); *A61K 36/35* (2013.01); *A61K 36/484* (2013.01); *A61K 36/539* (2013.01); *A61K 36/605* (2013.01); *A61K 36/61* (2013.01); *A61K 36/64* (2013.01); *A61K 36/65* (2013.01); *A61K 36/714* (2013.01); *A61K 36/718* (2013.01); *A61K 36/736* (2013.01); *A61K 36/75* (2013.01); *A61K 36/752* (2013.01); *A61K 36/756* (2013.01); *A61K 36/88* (2013.01); *A61K 36/884* (2013.01); *A61K 36/8988* (2013.01); *A61K 2236/37* (2013.01)

(58) Field of Classification Search
CPC ...... A61K 36/324; A61K 36/07; A61K 36/11; A61K 36/13; A61K 36/21; A61K 36/232; A61K 36/233; A61K 36/236; A61K 36/237; A61K 36/258; A61K 36/284; A61K 36/286; A61K 36/328; A61K 36/35; A61K 36/484; A61K 36/539; A61K 36/605; A61K 36/61; A61K 36/64; A61K 36/65; A61K 36/714; A61K 36/718; A61K 36/736; A61K 36/75; A61K 36/752; A61K 36/756; A61K 36/88; A61K 36/884; A61K 36/8988; A61K 2236/37

See application file for complete search history.

(56) References Cited

PUBLICATIONS

Wei-De Cheng, "Treatment of Glioblastoma Multiforme with (Yu Sheng) Ru Mo Si Wu Tang Variant", JCMAS vol. 7, No. 1, Dec. 2019, pp. 083-093.

*Primary Examiner* — Aaron J Kosar
(74) *Attorney, Agent, or Firm* — Bacon & Thomas, PLLC

(57) ABSTRACT

The present invention relates to a method for treating glioblastoma multiforme including administering a Chinese medicine composition to a subject in need thereof; wherein the Chinese medicine composition is an extract of a first mixture including *Boswellia sacra, Commiphora molmol, Angelica sinensis, Ligusticum striatum, Rehmannia glutinosa, Paeonia veitchii, Prunus persica,* and *Carthamus tinctorius.*

16 Claims, No Drawings

METHOD FOR TREATING GLIOBLASTOMA MULTIFORME

BACKGROUND OF THE INVENTION

1. Field of the Invention

The present invention relates to a method for treating glioblastoma multiforme.

2. Description of Related Art

Due to the potential of Chinese herbal medicine for treating cancer, traditional Chinese herbal medicine has gradually attracted attention in recent years. The principle of applying Chinese herbal medicine is based on the practice of traditional Chinese medicine theory.

Glioblastoma multiforme (GBM) is one of the most malignant brain tumors. Such brain tumor has characteristics including rapid growth, poor differentiation, internal necrosis, angiogenesis, low treatment rate, and high risk of recurrence. Compared to malignant cancers of other tissues or organs, GBM is less likely to metastasize out of the brain.

The current treatment for GBM is surgical resection, radiotherapy, oral chemotherapy drugs (Temodal), interstitial therapy, Tomo therapy, and the like. Although the aforementioned therapies can effectively alleviate the conditions of GBM, the patients cured after receiving said therapy seldom survive for more than 3 years. Therefore, there is an urgent need to provide a new therapeutic drug for patients with GBM to alleviate patients having GBM, improve their quality of life, or prolong their survival time.

SUMMARY OF THE INVENTION

The present invention relates to a composition and method for treating glioblastoma multiforme, which can alleviate glioblastoma multiforme, improve the patient's quality of life or prolong the patient's survival time.

The present invention provides a Chinese medicine composition for treating glioblastoma multiforme, comprising an extract of a first mixture comprising *Boswellia sacra*, *Commiphora molmol*, *Angelica sinensis*, *Ligusticum striatum*, *Rehmannia glutinosa*, *Paeonia veitchii*, *Prunus persica*, and *Carthamus tinctorius*.

The present invention further provides a method for treating glioblastoma multiforme, comprising: administering said Chinese medicine composition to a subject in need thereof. Specifically, an effective amount of said Chinese medicine composition is administered to the subject in need thereof.

The Chinese medicine composition may be prepared by the following steps: providing the first mixture; mixing the first mixture with water to form a second mixture; heating the second mixture to obtain a crude extract; and filtering the crude extract to keep a liquid extract and obtain the Chinese medicine composition.

The first mixture of the present invention may comprise 2-10 parts by weight of *Boswellia sacra*, 2-10 parts by weight of *Commiphora molmol*, 2-4 parts by weight of *Angelica sinensis*, 2-4 parts by weight of *Ligusticum striatum*, 2-4 parts by weight of *Rehmannia glutinosa*, 2-4 parts by weight of *Paeonia veitchii*, 2-4 parts by weight of *Prunus persica*, and 1-3 parts by weight of *Carthamus tinctorius*.

The first mixture of the present invention may further comprise at least one ingredient selected from the group consisting of *Dipsacus asperoides*, *Davallia mariesii*, *Achyranthes bidentate*, *Scutellaria baicalensis*, *Coptis teeta*, *Phellodendron amurense*, *Poria cocos*, *Alisma plantago-aquatic*, *Polyporus umbellatus*, *Atractylodes lancea*, *Gastrodia elata*, *Tetradium ruticarpum*, *Ephedra sinica*, *Notopterygium incisium*, *Bupleurum falcatum*, *Citri reticulatae pericarpium*, *Anredera cordifolia*, *Panax ginseng*, *Aconitum carmichaeli*, *Pimenta officinalis*, *Morus alba*, and *Glycyrrhiza uralensis*.

The first mixture of the present invention may further comprise at least one ingredient selected from the group consisting of 8-30 parts by weight of *Dipsacus asperoides*, 8-30 parts by weight of *Davallia mariesii*, 8-30 parts by weight of *Achyranthes bidentate*, 6-30 parts by weight of *Scutellaria baicalensis*, 4-30 parts by weight of *Coptis teeta*, 4-30 parts by weight of *Phellodendron amurense*, 4-30 parts by weight of *Poria cocos*, 4-20 *Alisma plantago-aquatica*, 3-5 parts by weight of *Polyporus umbellatus*, 2-5 parts by weight of *Atractylodes lancea*, 5-20 parts by weight of *Gastrodia elata*, 5-15 parts by weight of *Tetradium ruticarpum*, 1-3 parts by weight of *Ephedra sinica*, 3-4 parts by weight of *Notopterygium incisium*, 4-6 parts by weight of *Bupleurum falcatum*, 3-5 parts by weight of *Citri reticulatae pericarpium*, 2-4 parts by weight of *Anredera cordifolia*, 2-4 parts by weight of *Panax ginseng*, parts 4-6 by weight of *Aconitum carmichaeli*, 4-6 parts by weight of *Pimenta officinalis*, 3-12 parts by weight of *Morus alba*, and 2-4 parts by weight of *Glycyrrhiza uralensis*.

The first mixture further of the present invention may comprise *Atractylodes lancea*, *Glycyrrhiza uralensis*, *Scutellaria baicalensis*, *Coptis teeta*, *Phellodendron amurense*, *Poria cocos*, *Alisma plantago-aquatica*, *Gastrodia elata*, and *Ephedra sinica*. In one aspect of the present invention, the first mixture may further comprise 2-5 parts by weight of *Atractylodes lancea*, 2-4 parts by weight of *Glycyrrhiza uralensis*, 6-30 parts by weight of *Scutellaria baicalensis*, 4-30 parts by weight of *Coptis teeta*, 4-30 parts by weight of *Phellodendron amurense*, 4-30 parts by weight of *Poria cocos*, 4-20 parts by weight of *Alisma plantago-aquatica*, 5-20 parts by weight of *Gastrodia elata*, and 1-3 parts by weight of *Ephedra sinica*.

The first mixture of the present invention may further comprise *Panax ginseng*, *Aconitum carmichaeli*, and *Pimenta officinalis*. In one aspect of the present invention, the first mixture may further comprise 2-4 parts by weight of *Panax ginseng*, 4-6 parts by weight of *Aconitum carmichaeli*, and 4-6 parts by weight of *Pimenta officinalis*.

The first mixture of the present invention may further comprise *Morus alba*. In one aspect of the present invention, the first mixture of the present invention further comprise 3-12 parts by weight of *Morus alba*.

In the present invention, the part by weight of the first mixture may be 2.5-5 gram per part, preferably 3-4 gram per part, more preferably 3.75 gram per part, but the present invention is not limited thereto.

In the present invention, the term "treat" or "treatment" used herein refers to administer a Chinese medicine composition of the present invention to a subject in need thereof, thereby inhibiting, curing, improving, healing, ameliorating, alleviating, changing, or affecting a disease or the tendency of a disease. For instance, the method of the present invention may be used to inhibit division, replication, proliferation, invasion or transmigration of glioblastoma multiforme.

In the present invention, the term "effective amount" used herein refers to a necessary dose leading to expected therapeutic effects in a subject treated, and it may be changed depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, thinner, dispersant, suspending agent, thickener, excipient or the combination thereof.

In the present invention, the term "acceptable" used herein means that it should be compatible with the Chinese medicine composition, preferably be able to stabilize the Chinese medicine composition, and cannot jeopardize the subject treated.

The present invention is not restrictive of the method for decocting Chinese medicine, and it can be implemented in any known manner. The present invention is not restrictive of the method for heating the Chinese medicine, and it can be implemented by any known method, such as direct heating and double-boiling.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Unless specified otherwise, all technical and scientific terms described in the specification and claims of the present invention are defined as follows. In the present invention, the singular term and "the", may refer to one or more objects, unless specified otherwise. In addition, the term "comprise" is an open-ended transition word which does not limit to the items listed. The foregoing paragraphs are only systematic references and should not be construed as limitations for the subject of the invention. Unless specified otherwise, the materials used in the present invention are commercially available and easy to obtain. Possible sources for obtaining the materials are listed below and it is exemplary only.

In the following preparation examples, the part by weight is 3.75 gram per part.

Preparation Example 1

Provide 3 parts by weight of *Boswellia sacra*, 3 parts by weight of *Commiphora molmol*, 3 parts by weight of *Angelica sinensis*, 3 parts by weight of *Ligusticum striatum*, 3 parts by weight of *Rehmannia glutinosa*, 3 parts by weight of *Paeonia veitchii*, 3 parts by weight of *Prunus persica*, and 1.5 parts by weight of *Carthamus tinctorius* to form a first mixture-1; mix the first mixture-1 with 1500 parts by weight of water to form a second mixture-1; decoct the second mixture-1 for 1 hour to form a crude extract being about 400 parts by weight; filter the crude extract and collect the filtrate to obtain a Chinese medicine composition-1 of the present preparation example.

Preparation Example 2

The first mixture-1 of Preparation Example 1 was added with 3 parts by weight of *Atractylodes lancea*, 3 parts by weight of *Glycyrrhiza uralensis*, 8-20 parts by weight of *Scutellaria baicalensis*, 5 parts by weight of *Coptis teeta*, 5 parts by weight of *Phellodendron amurense*, 5 parts by weight of *Poria cocos*, 5 parts by weight of *Alisma plantago-aquatica*, 8-12 parts by weight of *Gastrodia elata*, and 2-2.5 parts by weight of *Ephedra sinica* to form a first mixture-2. Then, extract the first mixture-2 in a manner similar to Preparation Example 1 to obtain a Chinese medicine composition-2 of the present preparation example.

Preparation Example 3

The first mixture-2 of Preparation Example 2 was added with 3 parts by weight of *Panax ginseng*, 5 parts by weight of *Aconitum carmichaeli*, and 5 parts by weight of *Pimenta officinalis* to form a first mixture-3. Then, extract the first mixture-3 in a manner similar to Preparation Example 1 to obtain a Chinese medicine composition-3 of the present preparation example. The addition of *Panax ginseng*, *Aconitum carmichaeli*, and *Pimenta officinalis* can increase cerebral perfusion pressure, in favor of cerebral collateral circulation, thereby protecting normal cells, increasing the metabolism of brain tumor necrotic cells, and promoting the regeneration of normal brain cells.

Preparation Example 4

The first mixture-3 of Preparation Example 3 was added with 5-18 parts by weight of *Coptis teeta* and 5-10 parts by weight of *Morus alba* to form a first mixture-4. Then, extract the first mixture-4 in a manner similar to Preparation Example 1 to obtain a Chinese medicine composition-4 of the present preparation example.

The addition of *Coptis teeta* and *Morus alba* can eliminate edema and brain cell inflammation, promote brain cell toxicity of necrotic tumors, and dissolve the blockage of cerebrovascular and lymphatic vessels caused by metabolic wastes.

Example 1

The patient with cerebellar medulloblastoma (WHD IV) of Example 1 had been performed with surgery.

A treatment of the present invention applied to the patient of Example 1 was described below. A daily dose of the Chinese medicine composition-2 of Preparation Example 2 was administered to the patient every day, wherein the daily dose of the Chinese medicine composition-2 of Preparation Example 2 was divided into aliquots for ter in die administration. A follow-up report indicated that the patient still took the Chinese medicine composition-2 as of the reporting date, and the tumor was alleviated completely.

Example 2

A postoperative chemotherapy and radiotherapy was performed in the patient with cerebellar medulloblastoma (WHD IV) of Example 2. In details, the patient was performed with a surgery, a radiotherapy ended in three months thereafter, and the patient then took Temozolomide (TMZ).

A treatment of the present invention applied to the patient of Example 2 was described below. A daily dose of the Chinese medicine composition-3 of Preparation Example 3 was administered to the patient every day, wherein the daily dose of the Chinese medicine composition-3 of Preparation Example 3 was divided into aliquots for ter in die administration. A follow-up report indicated that the patient still took the Chinese medicine composition-3 as of the reporting date, and the tumor was alleviated completely.

Example 3

A postoperative chemotherapy and radiotherapy was performed in the patient with cerebellar medulloblastoma (WHD IV) of Example 3, and the patient was complicated with diabetes. In details, the patient was performed with a surgery and the radiotherapy ended in three months thereafter, and the patient then took Temozolomide (TMZ).

A treatment of the present invention applied to the patient of Example 3 was described below. A daily dose of the Chinese medicine composition-4 of Preparation Example 4 was administered to the patient every day, wherein the daily dose of the Chinese medicine composition-4 of Preparation Example 4 was divided into aliquots for ter in die administration. A follow-up report indicated that the patient still took the Chinese medicine composition-4 as of the reporting date, and the patient's blood sugar level was back to normal. In addition, the patient's tumor was alleviated completely, and the complication caused by the chemotherapy and radiotherapy were gone.

Although the present invention has been explained in relation to its preferred embodiment, it is to be understood that many other possible modifications and variations can be made without departing from the spirit and scope of the invention as hereinafter claimed.

What is claimed is:

1. A method for treating glioblastoma multiforme, comprising:
   administering a Chinese medicine composition to a subject in need thereof; wherein the Chinese medicine composition is an extract of a first mixture comprising *Boswellia sacra*, *Commiphora molmol*, *Angelica sinensis*, *Ligusticum striatum*, *Rehmannia glutinosa*, *Paeonia veitchii*, *Prunus persica*, and *Carthamus tinctorius*.

2. The method of claim 1, wherein the Chinese medicine composition is prepared by the following steps:
   providing the first mixture;
   mixing the first mixture with water to form a second mixture;
   heating the second mixture to obtain a crude extract; and
   filtering the crude extract to keep a liquid extract and obtain the Chinese medicine composition.

3. The method of claim 1, wherein the first mixture comprises 2-10 parts by weight of *Boswellia sacra*, 2-10 parts by weight of *Commiphora molmol*, 2-4 parts by weight of *Angelica sinensis*, 2-4 parts by weight of *Ligusticum striatum*, 2-4 parts by weight of *Rehmannia glutinosa*, 2-4 parts by weight of *Paeonia veitchii*, 2-4 parts by weight of *Prunus persica*, and 1-3 parts by weight of *Carthamus tinctorius*.

4. The method of claim 3, wherein the part by weight of the first mixture is 2.5-5 gram per part.

5. The method of claim 3, wherein the first mixture further comprises 2-5 parts by weight of *Atractylodes lancea*, 2-4 parts by weight of *Glycyrrhiza uralensis*, 6-30 parts by weight of *Scutellaria baicalensis*, 4-30 parts by weight of *Coptis teeta*, 4-30 parts by weight of *Phellodendron amurense*, 4-30 parts by weight of *Poria cocos*, 4-20 parts by weight of *Alisma plantago-aquatica*, 5-20 parts by weight of *Gastrodia elata*, and 1-3 parts by weight of *Ephedra sinica*.

6. The method of claim 5, wherein the first mixture further comprises 2-4 parts by weight of *Panax ginseng*, 4-6 parts by weight of *Aconitum carmichaeli*, and 4-6 parts by weight of *Pimenta officinalis*.

7. The method of claim 6, the first mixture further comprises 3-12 parts by weight of *Morus alba*.

8. The method of claim 1, wherein the first mixture further comprises at least one ingredient selected from the group consisting of *Dipsacus asperoides*, *Davallia mariesii*, *Achyranthes bidentate*, *Scutellaria baicalensis*, *Coptis teeta*, *Phellodendron amurense*, *Poria cocos*, *Alisma plantago-aquatic*, *Polyporus umbellatus*, *Atractylodes lancea*, *Gastrodia elata*, *Tetradium ruticarpum*, *Ephedra sinica*, *Notopterygium incisium*, *Bupleurum falcatum*, *Citri reticulatae pericarpium*, *Anredera cordifolia*, *Panax ginseng*, *Aconitum carmichaeli*, *Pimenta officinalis*, *Morus alba*, and *Glycyrrhiza uralensis*.

9. The method of claim 8, wherein the first mixture further comprises at least one ingredient selected from the group consisting of 8-30 parts by weight of *Dipsacus asperoides*, 8-30 parts by weight of *Davallia mariesii*, 8-30 parts by weight of *Achyranthes bidentate*, 6-30 parts by weight of *Scutellaria baicalensis*, 4-30 parts by weight of *Coptis teeta*, 4-30 parts by weight of *Phellodendron amurense*, 4-30 parts by weight of *Poria cocos*, 4-20 *Alisma plantago-aquatic*, 3-5 parts by weight of *Polyporus umbellatus*, 2-5 parts by weight of *Atractylodes lancea*, 5-20 parts by weight of *Gastrodia elata*, 5-15 parts by weight of *Tetradium ruticarpum*, 1-3 parts by weight of *Ephedra sinica*, 3-4 parts by weight of *Notopterygium incisium*, 4-6 parts by weight of *Bupleurum falcatum*, 3-5 parts by weight of *Citri reticulatae pericarpium*, 2-4 parts by weight of *Anredera cordifolia*, 2-4 parts by weight of *Panax ginseng*, parts 4-6 by weight of *Aconitum carmichaeli*, 4-6 parts by weight of *Pimenta officinalis*, 3-12 parts by weight of *Morus alba*, and 2-4 parts by weight of *Glycyrrhiza uralensis*.

10. The method of claim 9, wherein the part by weight of the first mixture is 2.5-5 gram per part.

11. The method of claim 1, wherein the first mixture further comprises *Atractylodes lancea*, *Glycyrrhiza uralensis*, *Scutellaria baicalensis*, *Coptis teeta*, *Phellodendron amurense*, *Poria cocos*, *Alisma plantago-aquatica*, *Gastrodia elata*, and *Ephedra sinica*.

12. The method of claim 11, wherein the first mixture further comprises *Panax ginseng*, *Aconitum carmichaeli*, and *Pimenta officinalis*.

13. The method of claim 12, wherein the first mixture further comprises *Morus alba*.

14. The method of claim 1, wherein the method is used to inhibit division, replication, proliferation, invasion or transmigration of glioblastoma multiforme.

15. The method of claim 1, wherein the Chinese medicine composition is administered via oral administration or injection.

16. The method of claim 1, wherein the Chinese composition further comprises pharmaceutically acceptable carrier, stabilizer, diluent, dispersant, suspending agents, thickening agent, excipient, or the combination thereof.

* * * * *